United States Patent [19]

Sachinvala

[11] Patent Number: 5,116,961
[45] Date of Patent: May 26, 1992

[54] 1',6,6'-TRIMETHACRYLOYL-2,3,3',4,4'-PENTA-O-METHYLSUCROSE

[75] Inventor: Navzer Sachinvala, Aiea, Hi.

[73] Assignee: Hawaiian Sugar Planters' Association, Aiea, Hi.

[21] Appl. No.: 697,983

[22] Filed: May 10, 1991

Related U.S. Application Data

[63] Continuation-in-part of Ser. No. 623,548, Dec. 7, 1990, abandoned.

[51] Int. Cl.⁵ .............................................. C07H 15/00
[52] U.S. Cl. .................. 536/18.2; 536/18.5; 536/120; 536/4.1
[58] Field of Search ............... 536/119, 120, 124, 126, 536/18.2, 18.5, 4.1

[56] References Cited

U.S. PATENT DOCUMENTS

| 4,002,609 | 1/1977 | Khan | 536/119 |
|---|---|---|---|
| 4,151,304 | 4/1979 | Evans | 514/777 |

FOREIGN PATENT DOCUMENTS 3535720  4/1987  Fed. Rep. of Germany .

OTHER PUBLICATIONS

"Pacific Polymer Peprints", vol. 1, (Nov. 1989) pp. 113-114, Dinikov.

Dirilikov, "Monomers and Poymers based on Mono- -and Dissaccharides", Pacific Polymer Preprints, vol. 1 (Dec. 12-15, 1989), pp. 113-114.

Hough et al., "Sucrochemistry, Part II,. 6,6'-Di-O-tritylsucrose", Carbohyd. Res., vol. 21 (1972), pp. 144-147.

Matsumoto et al., "Gelatin in the Copolymerization of Methyl Methacrylate with Trimethyolpropane Trimethacrylate", Eur. Polym. J., vol. 25, No. 4 (1989) pp. 385-389.

O'Donnell et al., "Synthesis of Some Partially Methylated Sucrose Derivatives", Aust. J. Chem., vol. 25 (1972), pp. 407-412.

Ogata et al., "Molecular Weight Control in Polycondensation of Hydroxyl Diesters with Hexamethylenediamine by Polymer Matrices", Journal of Polymer Science: Polymer Chemistry Edition, vol. 19 (1981), pp. 2609-2617.

Primary Examiner—Johnnie R. Brown
Assistant Examiner—Anita Varma
Attorney, Agent, or Firm—Burns, Doane, Swecker & Mathis

[57] ABSTRACT

A 1',6,6'-trimethylacryloyl-2,3,3',4,4'-penta-O-methylsucrose compound is disclosed. This compound is prepared by treating 2,3,3',4,4'-penta-O-methylsucrose with methacryloyl chloride in the presence of triethylamine and tetrahydrofuran. This compound is used as a crosslinking agent in the preparation of polymers.

2 Claims, 9 Drawing Sheets

1',6,6'-TRIMETHACRYLOYL-2,3,3',4,4'-PENTA-O-METHYLSUCROSE

GRANT REFERENCE

The invention described herein was partially funded by U.S.D.A. (A.R.S.) grant number 58-91H2-0-319.

This application is a continuation-in-part of U.S. application Ser. No. 07/623,548, filed Dec. 7, 1990, now abandoned.

BACKGROUND OF THE INVENTION

1. Field of the Invention

The present invention relates to a compound having the following structure (I):

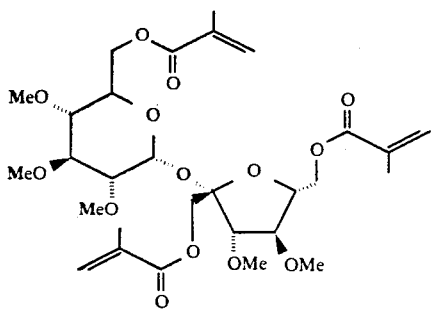

The compound of structure (I) is a trifunctional crosslinking agent which can be added in the presence of other vinyl monomers such as acrylic acid, methacrylic acid, alkyl acrylate, alkyl methacrylate or any other monomer containing a double bonded carbon and then polymerized.

2. Description of the Prior Art

In the past, many attempts have been made to employ carbohydrates for the development of well-characterized novel polymers of some practical significance. The use of sugars and their derivatives in the production of polymers is of growing interest since polymers containing mono- or disaccharides in their main chain or as grafted pendant groups or chains display useful and unique properties such as hydrophilicity, chirality, biological activity, biodegradability, and the like. Furthermore, most sugars are available at economical prices and are industrially produced in large quantities by cultivation in plants and microorganisms, followed by chemical isolation or by degradation of plant waste material followed by isolation. For instance, sucrose is produced on a scale that is larger than any other pure organic chemical, world-wide.

The major problem associated with the use of carbohydrates for developing polymers is the similar reactivity of the primary and secondary hydroxyl groups on the carbohydrate moiety. Hence, when carbohydrates are polymerized non-enzymatically with other monomers, the resulting polymer products are often a mixture of linear, cross-linked and branched chain products. This is due to the reaction of both the primary and secondary hydroxyl groups in the carbohydrate moiety with electrophilic groups in the other monomer.

Many attempts have been made in the past towards polymerizing carbohydrates such as those attempts described by N. Ogata et al. in *J. Polym. Sci., Polym. Chem. Ed.*, Vol. 19, p. 2609 (1981) and Vol. 22, p. 739 (1984); and S. K. Dirlikov, "Monomers and Polymers Based on Mono and Disaccharides", Pacific Polymer Preprints, First Pacific Polymer Conference, December 12-15, 1989, Volume 1, pp. 113-114.

Although Dirlikov, supra, claims that high molecular weight polymers have been made, no proof has been shown that these polymers are strictly linear and do not contain additional cross-linked or branched chain polymers and that only the primary hydroxyl groups react thereby forming a strictly linear polymer.

Sucrose used as a starting carbohydrate for the production of carbohydrate polymers would be ideal since it is produced in vast quantities and is low in price. To synthesize intermediate sucrose derivatives for further use in the production of novel polymers using sucrose as a starting compound is difficult due to the reactivity of the primary hydroxyl groups at carbons 6, 1' and 6' and the remaining five secondary hydroxyl groups.

One such sucrose intermediate is 2,3,3',4,4'-penta-O-methylsucrose having the structure (II)

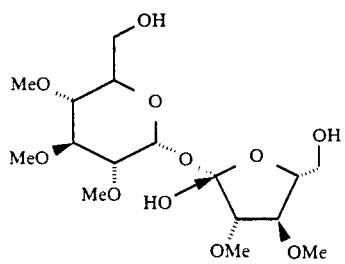

The compound of structure (II) is useful as an intermediate in the synthesis of other sucrose derivatives that can be used to synthesize various crosslinking agents.

Molecules such as glycerol, sorbitol, 3,5-dihydroxymethylbenzyl alcohol and pentaerythritol are examples of polyfunctional crosslinking agents, in addition to the more commonly used trifunctional crosslinking agent known as 2-ethyl-2-hydroxymethyl-1,3'propanediol or trimethylolpropanetriol. These polyols are traditionally known to crosslink polyesters or may be functionalized further to produce other polyfunctional crosslinking agents. Thus upon treatment of 2-ethyl-2-hydroxymethyl-1,3-propanediol with acryloyl or methacryloyl chloride the well known acrylic and methacrylic crosslinking agents, namely 2-ethyl-2-hydroxymethyl-1,3-propanediol triacrylate and 2-ethyl-2-hydroxymethyl-1,3-propanediol trimethacrylate are obtained. These crosslinking agents are commonly called trimethylolpropane triacrylate (TMPTA) and trimethylolpropane trimethacrylate (TMPTMA), respectively. Treatment of such an acrylate or methacrylate crosslinking agent with excess methyl acrylate or methyl methacrylate in the presence of a free radical initiator permits polymerization of these molecules to thermoset materials. However, due to the size of trimethylolpropane triacrylate or trimethacrylate and the symmetry of these molecules, only a small separation exists between the reactive ends of the acryloyl or methacryloyl moieties. Hence, some termini cross link the polymerizing methyl acrylate or methyl methacrylate and other termini internally cyclize to create ten-membered rings. In this situation the double bonds of the crosslinking agents are unused.

This internal cyclization or unused double bonds in the crosslinking agent reduces the networking ability of the crosslinking agents. For instance, it is described in Matsumoto et al "Gelation in the copolymerization of methyl methacrylate with trimethylolpropane trimethacrylate," *Eur. Polym. J.*, 25(4), 385-389 (1989) that the crosslinking efficiency of trimethylolpropane trimethacrylate is only 18% and that 82% of the polymer mixture had internally cyclized despite the fact that an excess of methyl methacrylate was present in the polymerizing milieu.

It has been surprisingly discovered that a trimethacryloyl-penta-O-methylsucrose, namely 1',6,6'-trimethacryloyl-2,3,3',4,4'-penta-O-methylsucrose can be prepared from the intermediate of structure (II) via a one step process and that this compound displays little internalization. This compound can be used as a crosslinking agent to strengthen the mechanical properties of various network methyl methacrylate polymers, in addition to polymeric networks created by other vinyl monomers polymerizing by a free radical mechanism.

OBJECTS AND SUMMARY OF THE PRESENT INVENTION

It is an object of the present invention to avoid or alleviate the problems of the prior art.

It is another object of the present invention to provide a novel compound of 1',6,6'-trimethacryloyl-2,3,3',4,4'-penta-O-methylsucrose.

It is another object of the present invention to provide a process for the synthesis of 1',6,6'-trimethacryloyl-2,3,3',4,4'-penta-O-methylsucrose.

It is another object of the present invention to provide a crosslinking agent that can be added to methyl methacrylate and other vinyl monomers and polymerized such that the final polymer is resistant to swelling, insoluble in any solvent and the mechanical properties of the methyl methacrylate polymer and other vinyl crosslinked polymers is enhanced.

Basically, the present invention features a compound having the following structure (I):

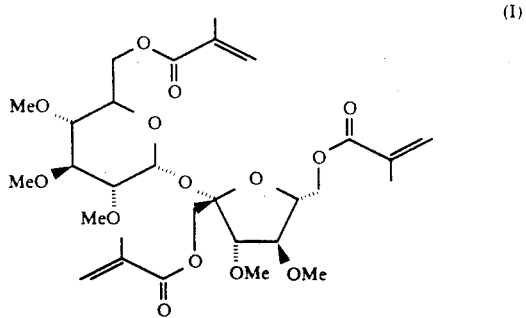

which compound is 1',6,6'-trimethylacryloyl-2,3,3',4,4'-penta-O-methylsucrose.

Another feature of the present invention is a method of using 1',6,6'-trimethylacryloyl-2,3,3',4,4'-penta-O-methylsucrose as a crosslinking agent in a polymer comprising mixing a vinyl monomer, the 1',6,6'-trimethyl-acryloyl-2,3,3',4,4'-penta-O-methylsucrose and a polymerization initiator to form a polymer and heating said polymer to a temperature between 110° C. to 120° C. after solidification.

DETAILED DESCRIPTION OF THE PREFERRED EMBODIMENTS OF THE PRESENT INVENTION

Figure 1:
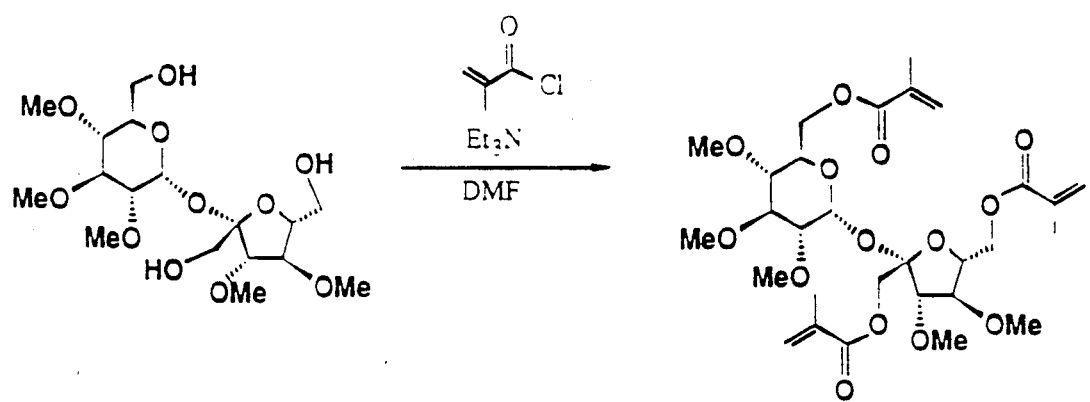
FIG. 1 is a diagrammatic representation of the synthesis of 1',6,6'-trimethacryloyl-2,3,3',4,4'-penta-O-methylsucrose.

More specifically, the present invention relates to the compound 1',6,6'-trimethylacryloyl-2,3,3',4,4'-penta-O-methylsucrose which is synthesized via a one step process. Generally, this process involves the addition of triethylamine to a solution of 2,3,3',4,4'-penta-O-methylsucrose in tetrahydrofuran at 0° C. to 4° C. followed by addition of methacryloyl chloride. After removal of the volatile contents in vacuo, the residue is reconstituted in hexanes: ethyl acetate (1:1) and filtered to remove the ammonium salts. The organic extract is then washed with dilute aqueous sodium bicarbonate to remove unreacted methacryloyl chloride, and the organic extract then dried over sodium sulfate. The extract is then filtered and concentrated in vacuo to provide an oil. The oil is then chromatographed on a column of silica gel using 20% ethyl acetate in hexanes to yield 1',6,6'-trimethacryloyl-2,3,3',4,4'-penta-O-methylsucrose.

2,3,3',4,4'-Penta-O-methylsucrose is prepared from sucrose in three steps. These steps include converting sucrose to 1',6,6'-tri-O-tritylsucrose, O-methylating the secondary hydroxyl groups and unmasking the triphenylmethyl(trityl) protecting groups by reduction with an alkali metal in liquid ammonia to form 2,3,3',4,4'-penta-O-methylsucrose.

The starting compound, sucrose, is first converted to 1',6,6'-tri-O-tritylsucrose by the reacting sucrose with trityl chloride. This method is described by Hough et al. in the journal *Carbohydrate Research*, Vol. 21 (1972), pp. 144-147, and is incorporated herein with some modifications. Specifically, the process involves the addition of trityl (triphenylmethyl) moieties to the 1', 6, and 6' positions on the sucrose molecule. The synthesis is performed by adding a solution of trityl chloride in dimethylformamide to a solution of sucrose in dimethylformamide and triethylamine. The amount of sucrose used may vary. For instance, between 314 mg (1 mmol) to 70 grams (204.5 mmol) of sucrose may be used. The amount of trityl chloride may also vary depending on the amount of starting sucrose used. For instance, about 4.5 times the molar amount of trityl chloride is used per mole of sucrose, and, therefore, it is preferable to use 260 grams (935 mmol) of trityl chloride per 70 grams (204.5 mmol) of sucrose. After dropwise addition of a solution of trityl chloride in dimethylformamide at 0° to 5° C. over a time period of about one hour, the mixture is allowed to warm to room temperature and then stirred at a constant temperature of about 45° C. for two days. The mixture is then concentrated to about half the original volume under reduced pressure and dissolved in methylene chloride, washed successively with water, 1 M hydrochloric acid, saturated aqueous sodium bicarbonate, water, and brine, and then dried in the presence of sodium sulfate. The methylene chloride is then removed in vacuo. The residue is then applied on a column of silica gel (230 to 400 mesh) and eluted successively with methylene chloride, 10% acetone in methylene chloride and 20% acetone in methylene chloride at a flow rate of about 100 ml/min. 100 ml fractions are collected and each fraction is spotted on a thin-layer chromatography plate, and the plate is developed with 20% acetone in methylene chloride. Three compounds elute from the column with methylene chloride and 10% acetone in methylene chloride. These three compounds are nonpolar compounds and typically have $R_f$ values of 0.83, 0.74, and 0.62 on silica gel 60 plates (0.25 mm, F-254 E. Merck). The desired 1',6,6'-tri-O-tritylsucrose elutes with 20% acetone in methylene chloride and has an $R_f$ value of 0.21 in 20% acetone in methylene chloride. The yield of 1',6,6'-tri-O-tritylsucrose using this method is typically between 65% and 70%.

The tri-O-tritylsucrose adduct is then O-methylated at positions 2,3,3',4 and 4' to produce 1',6,6'-tri-O-trityl-2,3,3',4,4'-penta-O-methylsucrose. The penta-O-methylation is performed under conditions that take advantage of the fact that a hydride base reacts rapidly with the secondary alcohols to produce hydrogen gas and the said alkoxides, without the possibility of reverting back to the alcohols. The alkoxides are then alkylated with an alkylating agent such as methyl iodide or dimethylsulfate to produce the penta-O-methyl ethers.

In the synthesis of the intermediate compound, 1',6,6'-tri-O-trityl-2,3,3',4,4'-penta-O-methylsucrose, all group (I) and group (II) metal hydrides, alkyl lithium, and aryl lithium bases, as well as all group (I) and group (II) bases can be used to convert the secondary alcohols to alkoxides. Examples include methyllithium, butyllithium, t-butyllithium, phenyllithium, sodium hydride, potassium hydride, and the like, to mention only a few. It is preferable to use a hydride base such as sodium hydride in the present process.

The amount of group (I) and group (II) metal hydrides and the aforementioned bases utilized in the second step of this process may vary depending on the amount of 1',6,6'-tri-O-tritylsucrose used in the reaction. For scales up to 10 mmol or 10.69 grams of tri-O-tritylsucrose, approximately 6 grams to 10 grams or 150 mmol to 250 mmol of a 60% dispersion of sodium hydride in oil are used. The presence of 3 to 5 equivalents of hydride base per reactive hydroxyl group in tri-O-tritylsucrose will ensure complete deprotonation of the alcohol to form the alkoxide, without the possibility of reverting back to the alcohol, provided no excess proton source is purposely introduced into the reaction mixture (i.e., by addition of water or other protic solvents). The excess sodium hydride is added to assure that the reaction mixture stays dry in case traces of moisture are accidentally introduced. If greater than 10 mmol of 1',6,6'-tri-O-tritylsucrose is reacted, i.e., 50 grams (46.76 mmol) to 150 grams (140 mmol), then an equal weight in grams of sodium hydride (60% in oil) is used. Thus, for instance, for 150 grams of tri-O-tritylsucrose, 150 grams (3900 mmol) of sodium hydride (60% dispersion in oil) is used. For large scale synthesis, it is preferable to use 5 equivalent excess of hydride ion for each hydroxyl group in tri-O-trityl-sucrose.

The hydride is usually stored as a dispersion in oil at varying concentrations. Prior to using the hydride base in the reaction, it should be washed free of the oil with pentane. Then the washed hydride is resuspended in a suitable solvent. Any polar aprotic solvent that can suspend or dissolve the hydride may be used, provided the solvent and hydride do not destructively react at the temperatures needed to deprotonate the alcohols. For example, dimethylformamide (DMF) begins to decompose in the presence of sodium hydride at 55° C. to 60° C. within a few hours to produce carbon monoxide and sodium dimethylamide. Examples of suitable hydrides and their corresponding solvent for this reaction include sodium hydride in DMSO, potassium hydride in DMSO at low temperatures of 0° to 40° C., sodium hydride in tetrahydrofuran (THF), potassium hydride in tetrahydrofuran (THF), sodium hydride in HMPA (hexamethylphosphoric triamide), sodium hydride in N-methylpyrrolidone, potassium hydride in N-methylpyrrolidone, sodium hydride in DMSO/THF, potassium hydride in DMSO/THF at low temperatures of 0° to 40° C., sodium or potassium hydrides in DMF at low temperatures of 0° to 40° C., calcium hydride in hexamethylphosphoric triamide, methyllithium, phenyllithium, butyllithium, sec-butyllithium or t-butyllithium in ether solvents such as tetrahydrofuran (THF), dioxane, dimethoxyoxyethane, diethylether or t-butylmethyl ether, alkyl lithium or aryl lithium and magnesium reagents in hexamethylphosphoric triamide or N-methylpyrrolidone, transition metal salts and hydrides of copper, cadmium, cobalt, and the like. It is preferable to use dimethylsulfoxide (DMSO) for a variety of reasons since methyl protons of DMSO are less acidic than the hydroxyl group protons of tri-O-tritylsucrose, DMSO does not completely react with sodium hydride to form the dimsylanion within 30 to 60 minutes at temperatures ranging between 25° C. to 55° C., and the red penta anion of tri-O-tritylsucrose is very soluble in DMSO. Moreover, since only small amounts of the dimsylanion is formed by using DMSO, the anion will react with the hydroxyl groups in tri-O-tritylsucrose to form alkoxides. The amount of solvent used in the present invention may vary depending upon the amount of tri-O-tritylsucrose and hydride used in the reaction. It is preferable to use 10 ml of DMSO per gram of tri-O-tritylsucrose or 0.1 M tri-O-tritylsucrose in DMSO.

The addition of the 1',6,6'-tri-O-tritylsucrose to the hydride base usually takes place at a temperature between 45° C. to 55° C. to permit the formation of alkoxides. It is preferable, however, that the reaction proceed at a temperature of about 50° C. to 60° C., most preferably about 50° C. The internal temperatures do not ever rise above 60° C.

This addition usually takes place over a period of 20 minutes to three hours depending on the amount of starting 1',6,6'-tri-O-tritylsucrose being used. For instance, if up to 10 mmol of the tritylsucrose is being reacted, then the addition takes place over a period of about 30 minutes. If the starting tritylsucrose concentration is greater than 10 mmol, then the addition to the hydride base may take up to 3 hours. The 1',6,6'-tri-O-tritylsucrose is added dropwise under constant stirring while the reaction temperature is monitored by placing a thermometer in the stirring vessel. After the addition of the tritylsucrose, the reaction mixture is maintained at the above-described temperature and constantly stirred for an additional time period. Usually this period is approximately 90 minutes.

After hydrogen evolution has ceased completely, a burgundy-red solution is obtained. This solution is then cooled to a temperature between 0° C. and 25° C.

Upon cooling the reaction mixture, an alkylating agent is then added dropwise over a varying time period, depending on the amounts of alkylating agents being added. For instance, in preparation containing up to 10 mmol of the tritylsucrose, the alkylating agent may be added over a period of about 30 minutes since less of the alkylating agent is used in the reaction. For preparations of larger than 10 mmol, the alkylating agent may be added over a time span of up to 90 minutes.

Any alkylating agent may be used in the present invention that will add an alkyl moiety to the alkoxide. Examples of the alkylating agents, which may be used in the present invention include methyl iodide, dimethyl sulfate, methyl chloride, methyl bromide, benzyl bromide, allyl bromide, octyl iodide, butyl iodide, halides and sulfonate esters of long chain hydrocarbons, and the like. If methyl iodide is used in this method, then it is usually freshly distilled over copper. The concentration of the alkylating agent may vary depending upon the amount of starting material present in the reaction medium. It is preferable to use a 5 molar equivalent excess of alkylating agent for each hydroxyl group in tri-O-tritylsucrose. Thus, for example, if 100 mmol of tri-O-tritylsucrose is used, 500 mmol of hydroxyl groups/100 mmol tri-O-tritylsucrose react and therefore 2,500 mmol of alkylating agent is used.

The alkylating agent is added over a period of time at a variety of temperatures, which depend upon the alkylating agent used. For instance, if methyl iodide is used, the reaction should be cooled to 0° C. and should not rise above 10° C. during the reaction. The addition of said alkylating agent should be very slow to preclude the internal temperature of the reaction from rising to the boiling point since the alkylating agent may evaporate. The reaction is then stirred at room temperature for a period between 2 to 24 hours. At this point, the mixture can be concentrated to one-fifth the volume at a temperature of about 60° C. under 0.1 mm Hg, if desired. Then the solution or concentrated solution is treated with a 10% solution of sodium hydroxide and stirred for an additional time period. After the addition of the sodium hydroxide, the resulting mixture is then diluted with water and an extracting agent such as methylene chloride or ethyl acetate. The extraction with the solvents is usually repeated at least twice, and the organic extracts are combined and further washed with water and brine. The washed organic extracts are then further dried over anhydrous magnesium sulfate, filtered, and concentrated in vacuo to provide a residue.

The residue is then placed over a silica gel column and the final product is eluted therefrom with a 1:1 hexane:methylene chloride solution of approximately 2 liters; followed by methylene chloride and 5% ethyl acetate in methylene chloride. The flow rate of the column varied between 100 ml/min to 200 ml/min.

The yield of 1',6,6'-tri-O-trityl-2,3,3',4,4'-penta-O-methylsucrose obtained by the above process is between 89% to 97%.

The 1',6,6'-tri-O-trityl-2,3,3',4,4'-penta-O-methylsucrose obtained is converted to 2,3,3',4,4'-penta-O-methylsucrose by unmasking the tri-O-trityl protecting groups to regenerate the hydroxyl groups at positions 1',6 and 6'. The trityl groups are removed by reduction without adversely effecting the glycosidic linkage. This reductive cleavage is performed by using alkali metals in the presence of liquid ammonia in a suitable aprotic solvent such as tetrahydrofuran (THF). Alternatively, the triphenylmethyl protecting groups may be removed by treatment of the tritritylpentamethyl adduct of sucrose with acetic acid. Here, the yields are low, possibly due to cleavage of sucrose to produce O-methylated glucose and fructose derivatives.

Any alkali metal can be used in the present procedure such as lithium, sodium and the like. Two alkali metals may also be used such as lithium and sodium. It is preferable, however, to use lithium in this reduction procedure, because it is relatively inexpensive, is less reactive than other group (I) metals in air, is safe to handle in air and is less pyrophoric than any other group (I) metals in the presence of moisture.

The tritylated penta-O-methylsucrose is diluted in tetrahydrofuran (THF) and liquid ammonia. It is preferable to use approximately 1 liter of tetrahydrofuran for every 100 grams of tri-O-trityl-penta-O-methylsucrose; however variations from this amount do not affect the yield of the final product. For example, 45 to 50 grams of tri-O-trityl- 2,3,3',4,4'-penta-O-methylsucrose can be dissolved in 1.0 liter of tetrahydrofuran (THF), or 288 grams of tri-O-trityl-2,3,3',4,4'-penta-methylsucrose can be dissolved in 2.5 liters of THF. If 288 grams (253 mmol) of 1',6,6'-tri-O-5 trityl-2,3,3',4,4'-penta-O-methylsucrose is dissolved in 2.5 liters of dry tetrahydrofuran, then the mixture is cooled to −70° C. Into this solution is distilled approximately 2.5 liters of liquid ammonia, and the mixture is treated with small pieces of lithium (12 grams, 1,714 mmol, 6.7 equivalent). It is preferable to use 2 to 5 equivalent excess of lithium for each millimole of triphenylmethyl group present in the molecule. It is more preferable to use a minimum of 2 equivalent excess alkali metal per mole of the trityl moiety. The addition of the alkali metal generally take place over a time period of 30 to 60 minutes depending upon the quantities involved. In this instance, the addition time is about 60 minutes. The color of the reaction mixture after addition of the alkali metal is deep red. The reaction mixture is allowed to stir for about three hours at a temperature between −65° C. to −78° C., more preferably at −70C. The excess alkali metal is then decomposed by the addition of ethanol or isopropanol. However, it is preferable to use ethanol, since it can be easily removed in vacuo. Approximately 1 ml of ethanol is added per millimole of alkali metal used. Small pieces of solid carbon dioxide ar also added after destroying the lithium metal to aid in the evaporation of ammonia as the solution is allowed to attain room temperature.

The resulting mixture is then filtered, the inorganic retentate is washed thoroughly with acetone, and the effluent is concentrated to a thick yellow oil. Flash column chromatography of the concentrated oil on a column of silica gel using 50% ethyl acetate in methylene chloride separates the triphenylmethane and other nonpolar components of the reaction mixture. 2,3,3',4,4'-Penta-O-methylsucrose is then eluted from the column with 10% ethanol in methylene chloride. The yield of the 2,3,3',4,4'-penta-O-methylsucrose from this isolation procedure is 95% to 97%.

After synthesizing 2,3,3',4,4'-penta-O-methylsucrose, it is further diluted in dry tetrahydrofuran at a temperature ranging from 0° C. to −10° C., preferably 0° C. Generally between 500 milligrams (1.21 mmol) to 33 grams (80 mmol) of 2,3,3',4,4'-penta-O-methylsucrose, preferably 3.88 grams (9.42 mmol) is diluted in dry tetrahydrofuran. The amount of dry tetrahydrofuran may vary depending on the amount of penta-O-methylsucrose used. For example if 1 mmol of penta-O-methylsucrose is used, then 10 ml of dry tetrahydrofuran is added thereto. It is preferably to use 100 ml of dry tetrahydrofuran for every 10 mmol of 2,3,3',4,4'-penta-O-methylsucrose.

Triethylamine is then added to this solution. The triethylamine is usually freshly distilled over sodium prior to its use and about 15 equivalents is added thereto. For example, if 3.88 grams of 2,3,3',4,4'-penta-O-methylsucrose is used, then 19.6 ml (141.3 mmol) of triethylamine is added. After adding the triethylamine, methacryloyl chloride, which is freshly distilled over a 3 angstrom molecular sieve, is then added dropwise. Additionally acryloyl chloride can be used instead of methacryloyl chloride. Generally between 4.5 equivalents to 6.0 equivalents of methacryloyl chloride or acryloyl chloride is added, but it is preferably to add 6 equivalents based on the amount of penta-O-methylsucrose used. The suspension is then further stirred between 0° C. and 8° C., preferably at 4° C. for about 3 hours. After this reaction period, the volatiles are then removed in vacuo at 4° C. and the residue is suspended in ethyl acetate in hexane (1:1), filtered to remove the ammonium salt and treated with an aqueous sodium bicarbonate solution. Following the usual workup and concentration in vacuo the residue is chromatographed on a silica gel column using 20% ethyl acetate in hexanes to provide 1',6,6'-trimethylacryloyl-2,3,3',4,4'-penta-O-methylsucrose as an oil. Yields in the synthesis of the 1',6,6'-trimethacrylates of 2,3,3',4,4'-penta-O-methyl-sucrose may vary between 45.6% to 60%.

1',6,6'-Trimethacryloyl-2,3,3',4,4'-penta-O-methylsucrose is a trifunctional crosslinking agent and can be added in small quantities to monomers containing double bonds such as vinyl monomers. These monomers include acrylic acid, methacrylic acid, methyl methacrylate, hydroxymethyl methacrylate, ethyl vinyl ether, styrene, and the like.

To produce a polymer with the crosslinking agent disclosed in the present invention, the vinyl monomer, cross-linking agent, and the polymerization initiator are mixed together, degassed, and set to polymerize at room temperature. Any sufficient initiator can be used in the present invention including any peroxide initiator, and the like. Subsequent to solidification of said polymer, the polymerization mixture is heated to a temperature from about 110° C. to 120° C. for about 1.5–4.0 hours, preferably 3 hours. The polymerized product is then equilibrated to room temperature prior to use.

In the case of 1',6,6'-trimethacryloyl-2,3,3',4,4'-penta-O-methylsucrose the possibility for any of the two methacryloyl moieties to intramolecularly cyclize in the presence of excess methyl methacrylate is remote because the distance between the reactive sites of the 6 and 6' methacryloyl moieties is 16 atoms; the reactive ends at the 1' and 6' positions are spaced apart by 12 atoms and these two positions with respect to each other are anti in orientation on the fructofuranosyl moiety; and the reactive ends at positions 1' and 6 are separated by 14 atoms and may experience considerable stearic hindrance during intramolecular cyclization owing to the presence of the 2,3,4-tri-O-methylglucopranosyl moiety between these two ends.

In order to further illustrate the present invention and the advantages thereof, the following specific examples are given, it being understood that same are intended only as illustrative and in nowise limitative

EXAMPLE 1

A. Synthesis of 1',6,6'-tri-O-tritylsucrose

The procedure of Hough, Mufti, and Khan, Carbohydrate Res., Vol. 21, pp. 144–147 (1972), is modified as shown below. To a solution of 15 g of sucrose (43.82 mmol) in 225 ml of pyridine, a solution of 54.95 g of trityl chloride (197.1 mmol, 4.5 equiv.) in 50 ml of pyridine is added dropwise over a period of 30 minutes. The reaction mixture is then stirred at room temperature for 4 days. After 4 days, the solution is concentrated to a brown syrup, which is dissolved in methylene chloride. This solution is further washed successively with 1 M hydrochloric acid, saturated sodium bicarbonate solution, water, and brine and then dried over anhydrous sodium sulfate. The methylene chloride solution is then concentrated in vacuo and the residue applied on a column of silica gel packed in methylene chloride:acetone (4:1) and eluted with that solvent. The 1',6,6'-tri-O-tritylsucrose is obtained (28.59 g) in 58.8% yield as an off-white solid with a melting point of 127° to 130° C.

B. Synthesis of 1',6,6'-tri-O-tritylsucrose

On scales larger than 40 mmol, the following procedure can be used. However, the yields established in the method shown are reproducible on scales ranging from 1 mmol to 21 mmol.

In a dry 5-L four-neck flask is dissolved 70 grams of sucrose (204.5 mmol) in 1 liter dry dimethylformamide (DMF) and dry triethylamine (200 ml, 145 grams, 1,423 mmol). The solution is allowed to attain a temperature of 25° to 30° C. and treated with a solution of trityl chloride (260 grams, 935.2 mmol, 4.5 equiv.) in dimethylformamide (600 ml), added dropwise over 1 hour. After the addition is complete, the reaction mixture is heated to a temperature of 50° C. and allowed to stir for 48 hours at that temperature. After 2 days, the reaction mixture is filtered through a short pad of silica gel to remove the precipitated triethylammonium hydrochloride and the residue is washed with methylene chloride:acetone (4:1). The effluent is then concentrated to a residue, which is reconstituted in methylene chloride and washed successively with 1 N hydrochloric acid, saturated sodium bicarbonate solution, water, and brine and then dried over anhydrous sodium sulfate. The dry organic extract is then filtered and concentrated in vacuo to provide a yellow foamy solid. This material is then applied on a silica gel column (230 to 400 mesh, 10 cm × 50 cm) packed with methylene chloride and successively eluted with methylene chloride, then 10% acetone in methylene chloride, followed by elution with 20% acetone in methylene chloride. The desired tri-O-tritylsucrose elutes with 20% acetone in methylene chloride and has an $R_f$ of 0.21 in the same solvent. The amount of 1',6,6'-tri-O-tritylsucrose obtained by this method of synthesis and isolation is typically between 146 to 150 grams or 67% to 68.8%. On scales between 1 mmol and 50 mmol (314 mg to 15.7 grams) yields average about 76%.

Figure 2:
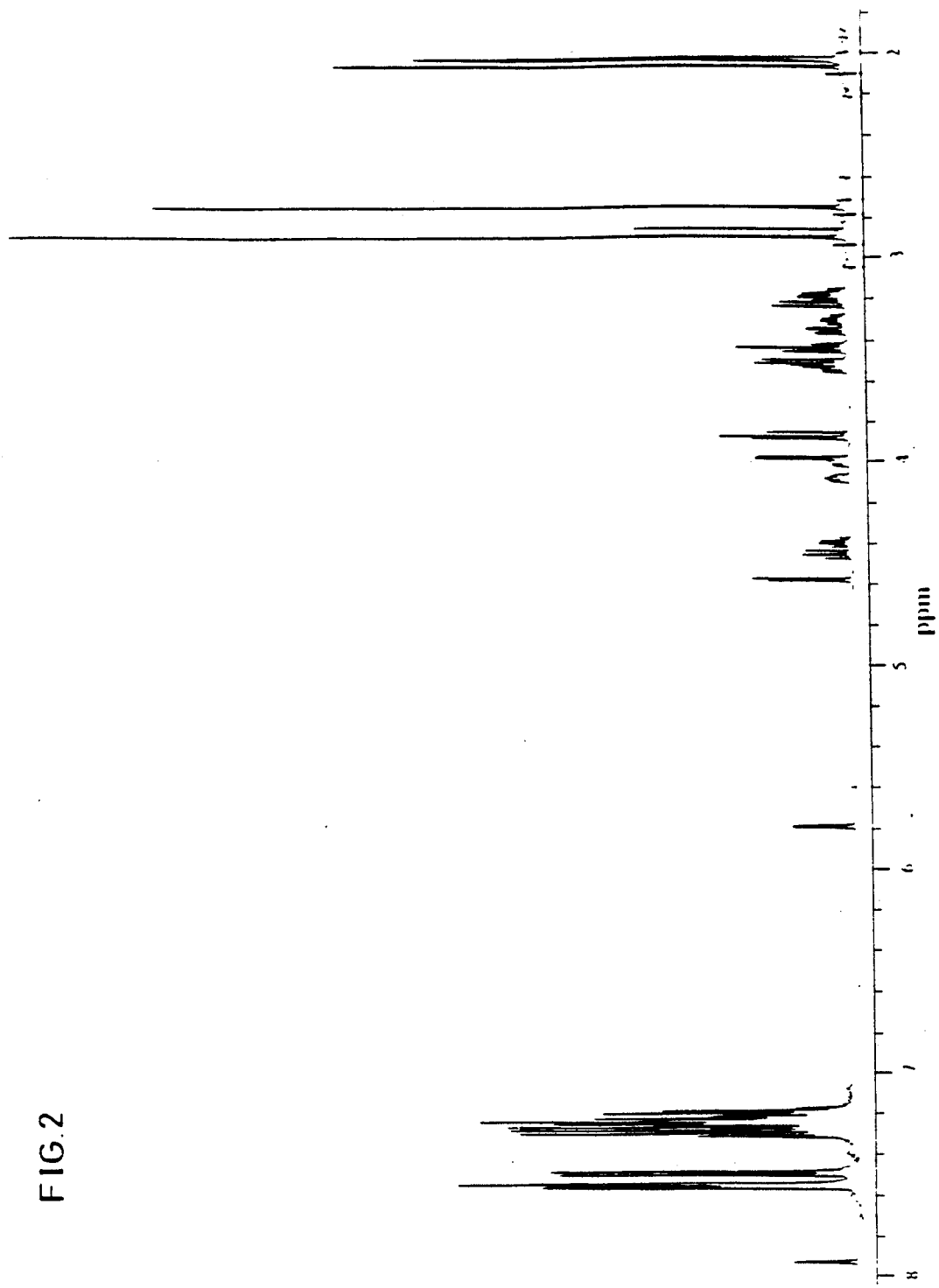
FIG. 2 is an $^1$H NMR spectrum of 1',6,6'-tri-O-tritylsucrose synthesized in the present invention.
Figure 3:
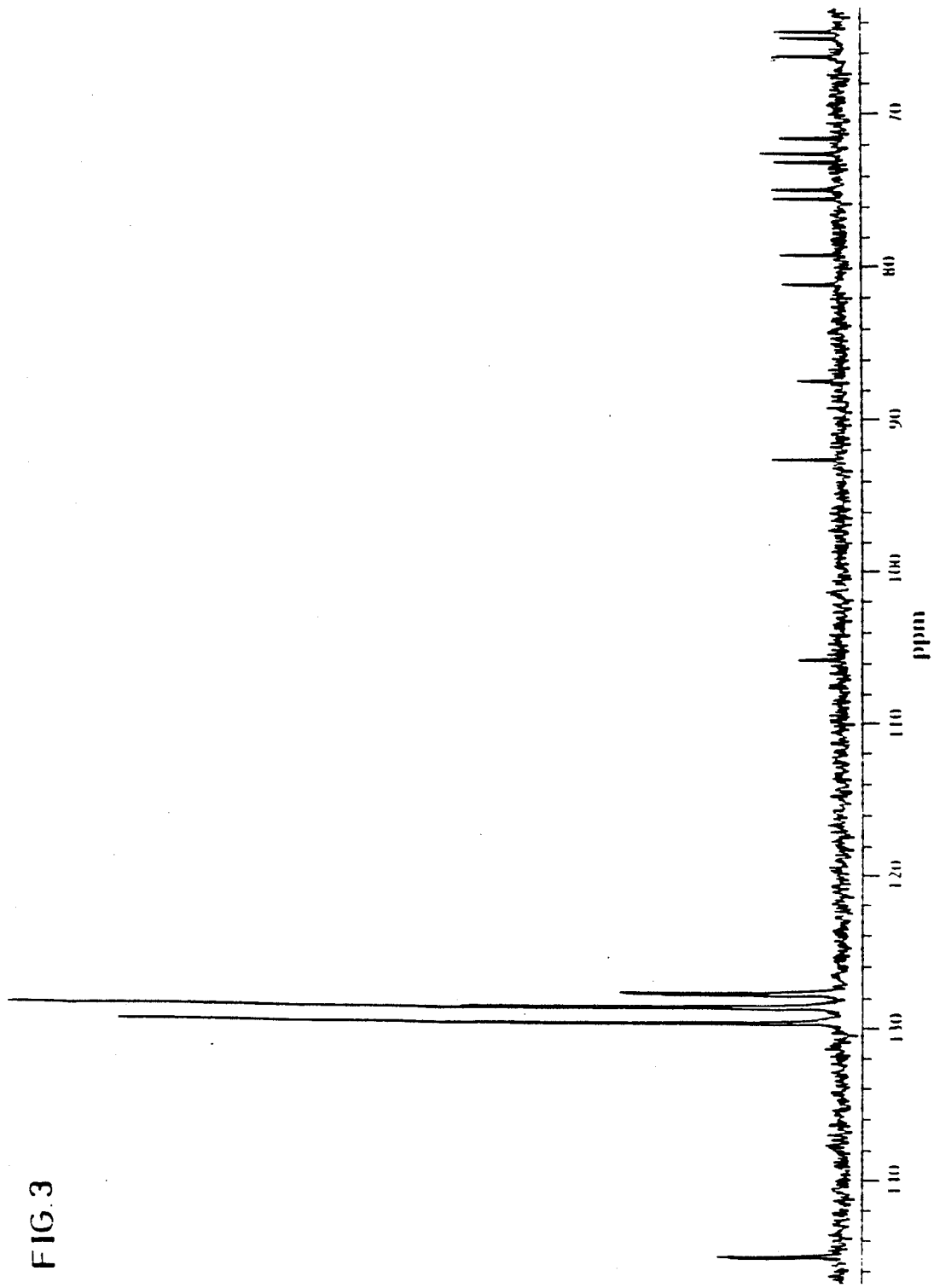
FIG. 3 is a $^{13}$C NMR spectrum of 1',6,6'-tri-O-tritylsucrose synthesized in the present invention.

FIGS. 2 and 3 illustrate the respective NMR spectra of 1',6,6'-tri-O-tritylsucrose.

C. Synthesis of 1',6,6'-tri-O-trityl-2,3,3',4,4'-penta-O-methylsucrose

Figure 4:
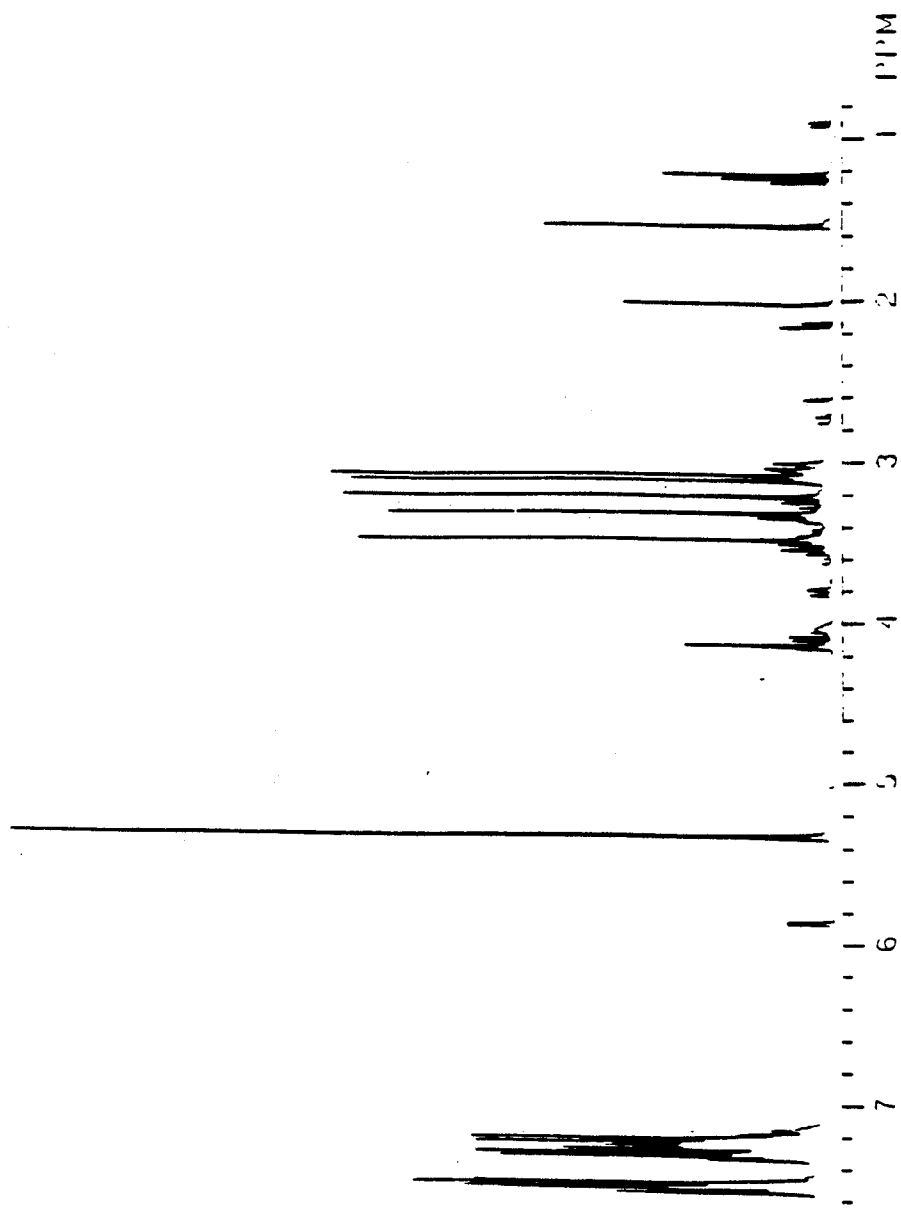
FIG. 4 is an $^1$H NMR spectrum of 1',6,6'-tri-O-trityl-2,3,3',4,4'-penta-O-methylsucrose synthesized in the present invention.
Figure 5:
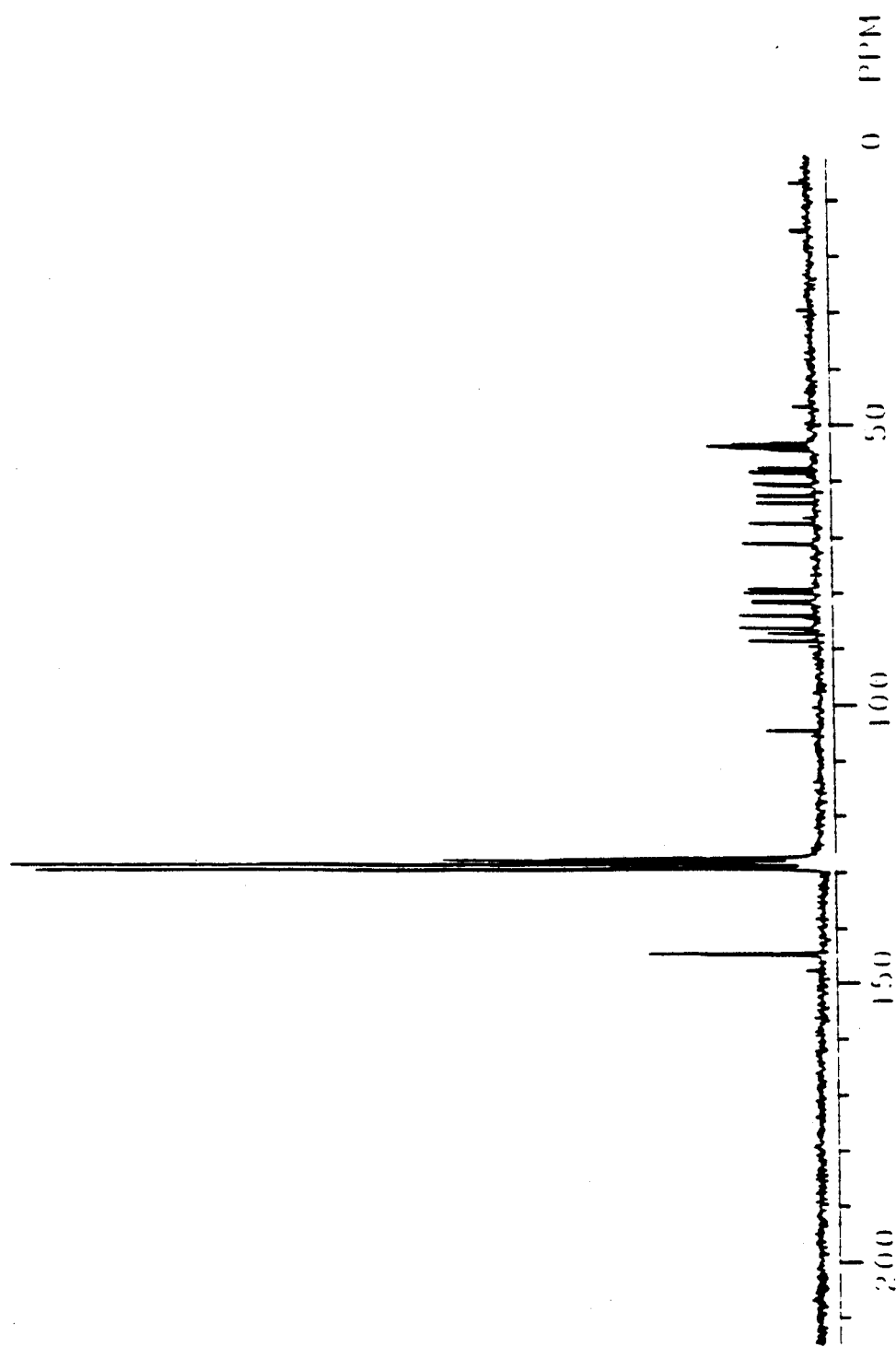
FIG. 5 is a $^{13}$C NMR spectrum of 1',6,6'-tri-O-trityl-2,3,3',4,4'-penta-O-methylsucrose synthesized in the present invention.

On scales larger than 10 mmol the following procedure is used. To a dry 5-L four-neck flask is added sodium hydride (60% in oil, 150 grams, 1250 mmol), washed free of oil with pentane and suspended in DMSO (800 ml). The suspension is heated to 50° C., mechanically stirred, and treated with a solution of 1,6,6'-tri-O-tritylsucrose (50 grams, 46.76 mmol, dissolved in DMSO 200 ml, and added dropwise over 2 hours). The temperature of the reaction is monitored internally and maintained between 50° C. and 55° C. during the course of addition and 90 minutes thereafter. After hydrogen evolution has ceased completely, the burgundy-red solution is cooled to 25° C. and treated with dimethyl sulfate (147.5 grams, 1175 mmol, 111 ml, added dropwise over 90 minutes). The reaction is stirred at room temperature for 24 hours, treated with aqueous sodium hydroxide (10% solution, 500 ml), and stirred for an additional 3 hours. The mixture is then diluted with water (500 ml) and methylene chloride (500 ml) and the phases separated. The aqueous layer is re-extracted with methylene chloride (4×300 ml), then the organic extracts are combined, washed with water and brine, dried over anhydrous magnesium sulfate, filtered, and concentrated in vacuo. The glassy residue is flash-chromatographed over a column of silica gel (10 cm×15 cm) and eluted with hexanes:methylene chloride (1:1, 2 L), then methylene chloride (2 L) followed by 5% ethyl acetate in methylene chloride (2 L), at a flow rate of about 200 ml/min. The isolated product (mp 103°–108° C.) weighed 47.1 grams (41.35 and a 89% yield is obtained. $R_f$ of the tritylated methylsucrose is 0.15 in methylene chloride and $[\alpha]_D^{27} = 47.68°$ in methylene chloride. FIGS. 4 and 5 illustrate the respective NMR spectra for this product. The NMR data provided: $^1$H NMR (500.11 MHz, acetone-$D_6$) δ3.04 (H-2, dd, J=3.5, 9.5 Hz), 3.06 (H-1'a, d, J=10 Hz), 3.07 (H-6a, dd, J=3, 10 Hz), 3.14 (OMe-3', s), 3.16 (OMe-4', s), 3.19 (OMe-2, s), 3.21 (H-3, t, J=9.5 Hz), 3.31 (OMe-4, s), 3.36 (H-1'b, d, J=10 Hz), 3.41 (OMe-3, s), 3.41 (H-6b, J=2, 10 Hz), 3.51 (H-6'a, m), 3.53 (H-4, dd, J=9.5, 10 Hz), 3.55 (H-6'b, m), 3.88 (H-5, dd, J=2, 3, 10 Hz), 4.17 (H-3, d, J=8.5 Hz), 4.29 (H-4', t, J=8.5 H), 4.41 (H-5', m), 5.98 (H-1, d, J=3.5 Hz), 7.34 (30H arom), 7.52 (15H arom). $^{13}$C NMR (125.76 MHz, acetone-$D_6$) δ57.73 (OMe-3'), 58.36 (OMe-4'), 58.68 (OMe-2), 60.46 (OMe-4), 60.60 (OMe-3), 62.97 ($CH_2$-6'), 63.89 ($CH_2$-6), 67.86 ($CH_2$-1'), 71.41 (CH-5), 79.52 (CH-5'), 80.17 (CH-4), 81.50 (CH-4'), 82.35 (CH-2), 84.52 (CH-3), 86.74 (1'-C-trityl methine), 86.93 (CH-3'), 87.51 (6-C-trityl methine), 87.68 (6'-C-trityl methine), 88.92 (CH-1), 104.66 (CH-2'), 127.22 (CH), 127.43 (2CH), 128.07 (2CH), 128.23 (3CH), 128.27 (CH), 129.03 (2CH), 129.14 (4CH), 144.05(C); 144.32 (2C); FAB mass for $C_{74}H_{74}O_{11}$ calculated 1138.33; found M$^+$+1=1139, M$^+$−H+K$^+$=1177, M$^+$+K$^+$=1178. Anal. Calc. for $C_{74}H_{74}O_{11}$: C, 78.0; H, 6.5; O, 15.5. Found: C, 77.5; H, 6.5.

After scale-up of this reaction employing 150 g tri-O-tritylsucrose (140 mmol), 150 g of sodium hydride (60% in oil, 3,900 mmol); 1,600 ml of dimethylsulfoxide; and 330 ml of dimethylsulfate (441 g, 3,500 mmol) was performed under exactly the same conditions discussed above. After chromatography on a column of silica gel (230 to 400 mesh. 10 cm×50 cm) and elution with three times the quantities of solvents discussed above, 145.15 g of tri-O-trityl-penta-O-methylsucrose was obtained in 91% yield.

D. Synthesis of 2,3,3',4,4'-penta-O-methylsucrose

To a 40 mmol solution of 1',6,6'-tri-O-trityl-2,3,3',4,4'-penta-O-methylsucrose (45.6 grams) in 1 liter of dry tetrahydrofuran and 2 liters of liquid ammonia at −70° C. is added 4 grams of small pieces of lithium wire. The lithium wire is added over a period of over 50 minutes and a deep-red solution is obtained. This solution is further stirred for 3 hours at −70° C. The excess lithium is decomposed by adding 60 ml of ethanol. Small pieces of solid carbon dioxide are also added to aid the evaporation of ammonia as the solution approaches room temperature. The resulting mixture is then filtered, and the inorganic retentate is washed thoroughly five times with 300 ml of acetone. The effluent is then concentrated to a thick yellow oil.

The product is then purified by flash column chromatography according to the guidelines of Still, Kahn and Mitra, J. Chem., Vol. 43 (1978), pp. 2923-2925, on 230–400 mesh silica gel.

The oil is then placed on a silica gel column (10 cm×15 cm) and is washed with a solution containing 50% ethyl acetate in methylene chloride at a flow rate of 200 ml/min. This wash separates out the triphenylmethane and other nonpolar components of the reaction mixture.

Figure 6:
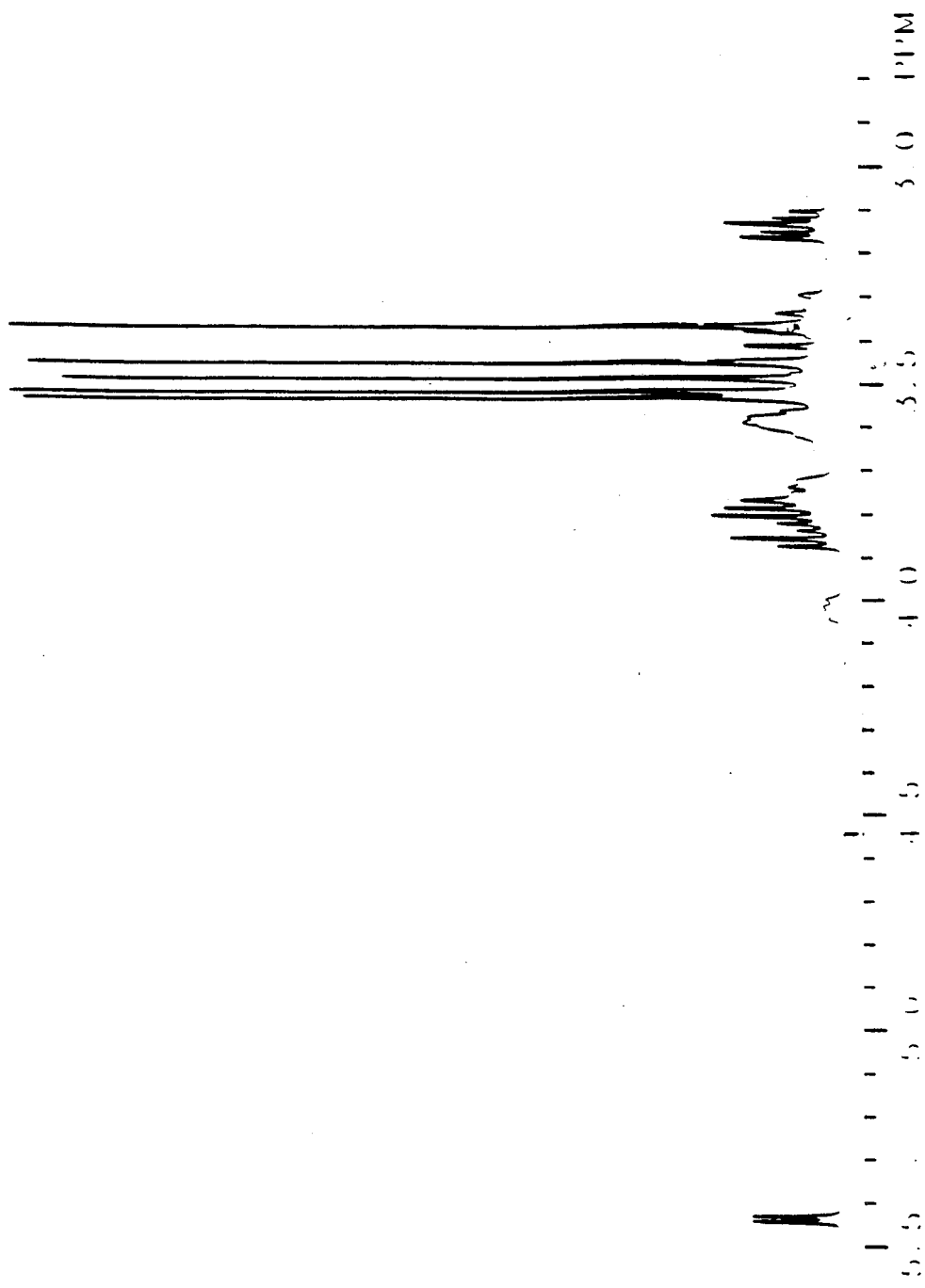
FIG. 6 is an $^1$H NMR spectrum of 2,3,3',4,4'-penta-O-methylsucrose synthesized in the present invention.
Figure 7:
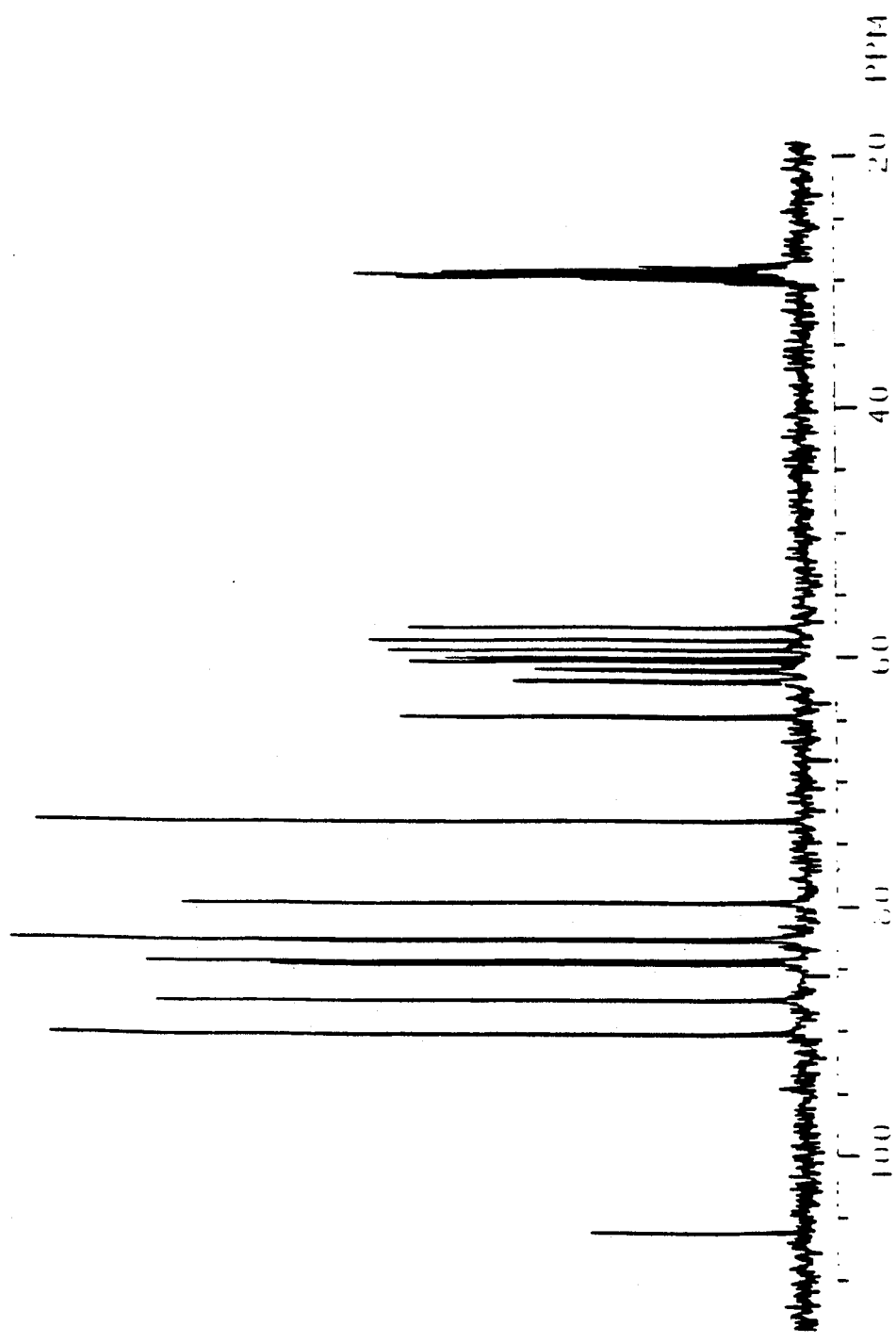
FIG. 7 is a $^{13}$C NMR spectrum of 2,3,3',4,4'-penta-O-methylsucrose synthesized in the present invention.

2,3,3',4,4'-Penta-O-methylsucrose is eluted from the column with a 10% ethanol in methylene chloride solution. 16.11 grams, 39.10 mmol of 2,3,3',4,4'-penta-O-methylsucrose is obtained, and the yield of this product is 97%. $R_f$ in 5% ethanol in methylene chloride is 0.31 and $[\alpha]_D^{27} = 50.60°$ in acetone. $^1$H NMR (500.11 MHz, acetone $D_6$) δ3.15 (H-4, t, $J_{3,4}$=9.8 Hz, $J_{4,5}$=9.0 Hz), 3.15 (H-2, dd, $J_{1,2}$=3.7 Hz, $J_{2,3}$=9.8 Hz), 3.33 (H-1'a, d, $J_{1'a,1'b}$=−12.5 Hz), 3.38 (OMe-4', s), 3.40 (H-3, t, $J_{3,4}$=9.8 Hz), 3.46 (OMe-3', s), 3.50 (OMe-2, s), 3.53 (OMe-4, s), 3.55 (OMe-3, s), 3.55 (H-1'b,d), 3.59 (H-6'a, m, $J_{6'a,6'b}$=12.0 Hz), 3.60 (H-6a, dd, $J_{5,6a}$=5 Hz, $J_{6a,6b}$=−10.6 Hz), 3.61 (H-6'b, m $J_{6'a,6'b}$=−12.0 Hz), 3.75 (H-6b, dd, $J_{5,6b}$=2.1 Hz, $J_{6a,6b}$=−10.6 Hz), 3.78 (H-5, m, $J_{5,6a}$=5 Hz, $J_{5,6b}$=2.1 Hz), 3.80 (H-4', t, $J_{3',4'}$=5.1 Hz, $J_{4',5'}$=5.8 Hz), 3.84 (H-5', m, $J_{5',6'a}$=4.2 Hz, $J_{5',6'b}$=6.3 Hz), 3.87 (H-3', d, $J_{3',4'}$=5.1 Hz), 5.45 (H-1, d, $J_{1,2}$=3.7 Hz). $^{13}$C NMR (125.76 MHz, acetone $D_6$) δ57.96 (OMe-4'), 58.98 (OMe-3'), 59.76 (OMe-2), 60.29 ($CH_2$-6), 60.39 (OMe-4), 60.67 (OMe-3), 61.79 ($CH_2$-6'), 64.63 ($CH_2$-1'), 73.12 (CH-5), 79.53 (CH-2), 82.48 (CH-4), 82.59 (CH-5'), 84.24 (CH-3), 84.52 (CH-4'), 87.48 (CH-3'), 90.17 (CH-1), 106.80 (C-2'). FDMS for $C_{17}H_{32}O_{11}$ calculated 412.43; found M+1=413. Anal. Calc. for $C_{17}H_{34}O_{11}$: C, 49.5; H, 7.5; O, 42.8. Found: C, 49.2; H, 7.8. FIGS. 6 and 7 illustrate the respective NMR spectra of 2,3,3',4,4'-penta-O-methylsucrose.

E. Synthesis of 1',6,6'-trimethylacryloyl-2,3,3',4,4'-penta-O-methylsucrose

Figure 8:
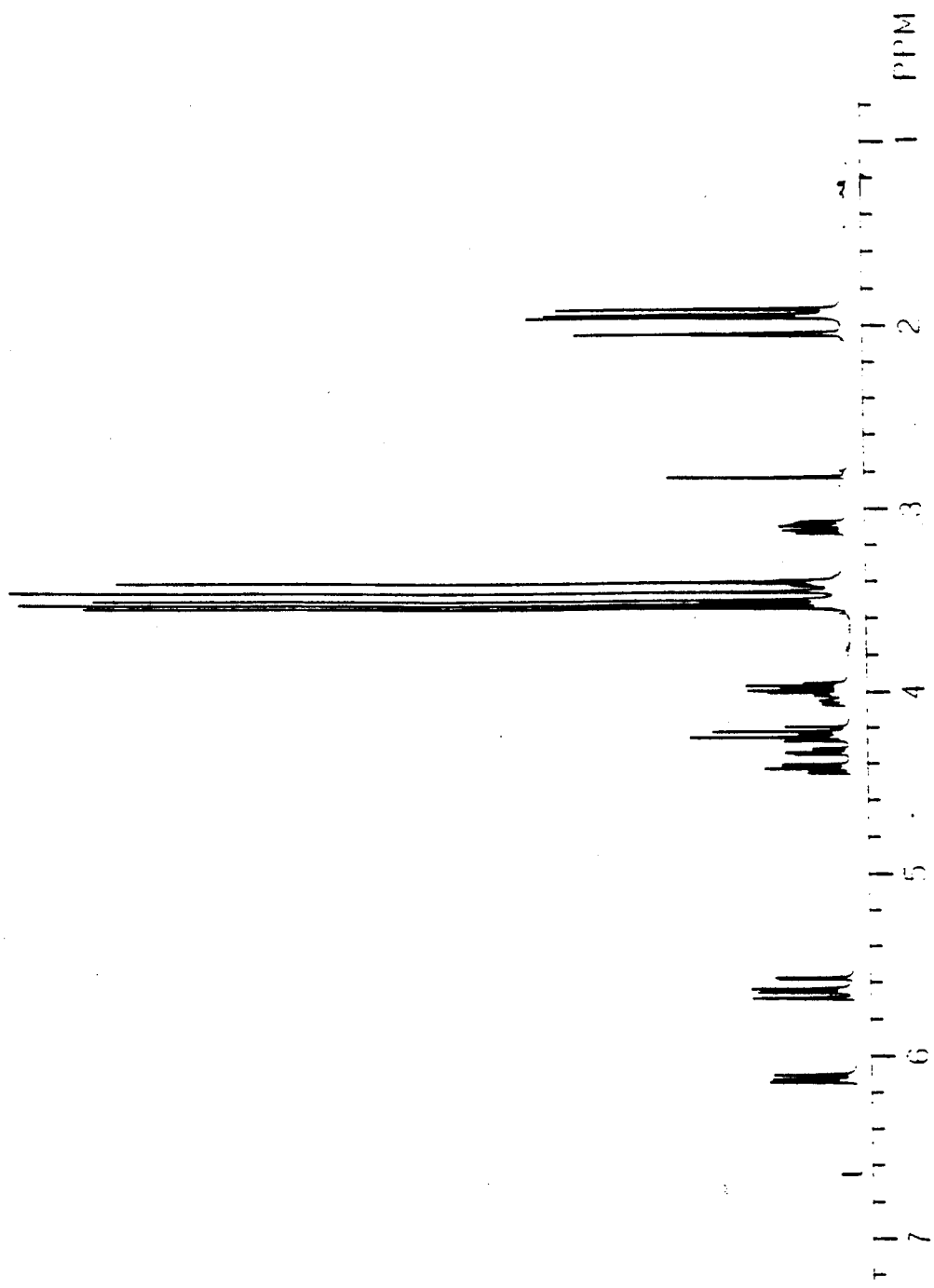
FIG. 8 is a $^1$H NMR spectrum of 1',6,6'-trimethacryloyl-2,3,3',4,4'-penta-O-methylsucrose synthesized in the present invention.
Figure 9:
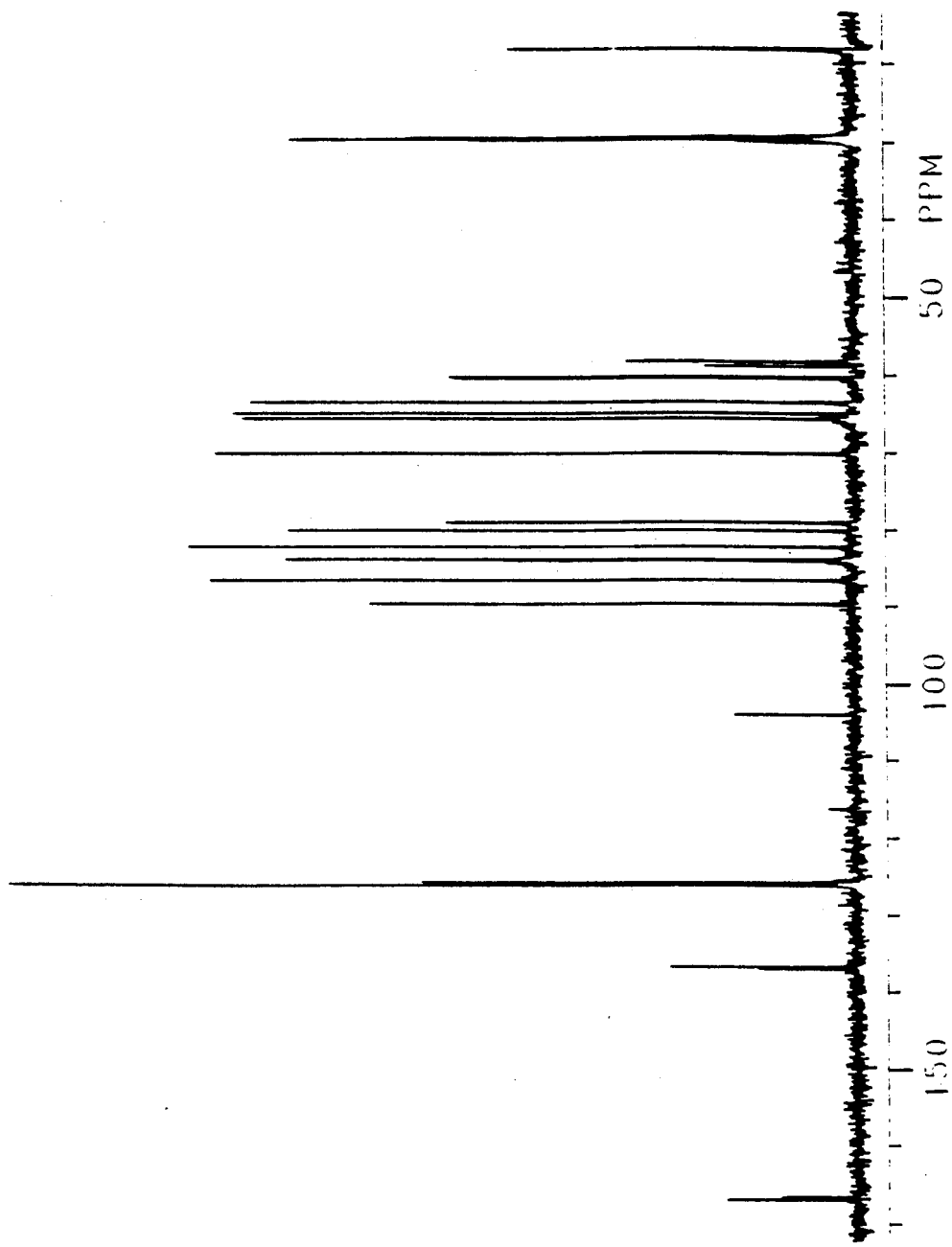
FIG. 9 is a $^{13}$C NMR spectrum of 1',6,6'-trimethacryloyl-2,3,3',4,4'-penta-O-methylsucrose synthesized in the present invention.

To a solution of 2,3,3',4,4'-penta-O-methylsucrose (3.88 g, 9.42 mmol) in dry tetrahydrofuran (100 ml) at 0° C. is added triethylamine (freshly distilled over sodium, 10 ml, 7.4 g, 73.3 mmol, 15 equivalents), followed by methacryloyl chloride (freshly distilled over 3 angstroms molecular sieves, 5.52 ml, 5.91 g, 56.5 mmol, 6 equivalents, added dropwise over 15 minutes). The suspension is stirred at 4° C. and monitored by thin-layer chromatography using 50% ethyl acetate in hexanes. After 3 hours at 4° C., the volatiles are removed in vacuo at 4° C., then the residue is redissolved in ethyl acetate in hexanes (1:1, 20 ml), filtered to remove the ammonium salt and treated with an aqueous sodium bicarbonate solution (0.2 M, 10 ml). Following concentration in vacuo, the residue is chromatographed on a silica gel column (5 cm × 15 cm) using 20% ethyl acetate in hexanes to provide 1',6,6'-trimethylacryloyl-2,3,3',4,4'-penta-O-methylsucrose as an oil (2.91 g, 4.71 mmol, 50% yield). $R_f$ of the product in 50% ethyl acetate in hexanes is 0.42, $[\alpha]_D^{26}=45.73$ in acetone. $^1$H NMR (500.11 MHz, acetone $D_6$) δ1.90 (3H, m, methacryloyl), 1.93 (3H, m, methacryloyl), 1.95 (3H, m, methacryloyl), 3.07 (H-2, dd, J=4.3, 9.5 Hz), 3.12 (H-4, t, J=9.5 Hz), 3.40 (OMe-2, s), 3.41 (H-3, t, J=9.5 Hz), 3.45 (OMe-3',s), 3.50 (OMe-4, s), 3.52 (OMe-4', s), 3.54 (OMe-3, s), 3.96 (H-4', t, J=7 Hz), 3.99 (H-3', d, J=7 Hz), 4.02 (H-5', ddd, J=4, 5.5, 7 Hz), 4.06 (H-5, ddd, J=2,5,10 Hz), 4.20 (H-1'a, d, J=12 Hz), 4.25 (H-1'b, d, J=12 Hz), 4.27 (H-6a, dd, J=5, 11.5 Hz), 4.33 (H-6'a, dd, J=5.5, 12 Hz), 4.41 (H-6'b, dd, J=4, 12 Hz), 4.43 (H-6b, dd, J=2, 11.5 Hz), 5.46 (H-1, d, J=4.3 Hz), 5.57 (1H, m), 5.63 (1H, m), 5.65 (1H, m), 6.09 (1H, m), 6.11 (1H, m), 6.14 (1H, m). $^{13}$C NMR (125.76 MHz, acetone $D_6$) δ18.09 (2CH$_3$ methacryloyl), 18.15 (CH$_3$ methaceyloyl), 58.21 (2CH$_3$, OMe-2, OMe-3'), 58.74 (OMe-4'), 60.21 (OMe-4), 60.39 (OMe-3), 63.53 (CH$_2$-6), 64.94 (CH$_2$-6'), 65.62 (CH$_2$-1'), 70.03 (CH-5), 78.87 (CH-5'), 79.93 (CH-4), 82.12 (CH-2), 83.82 (CH-3), 83.96 (CH-3'), 86.54 (CH-4'), 89.59 (CH-1), 103.84 (CH-2'), 125.49 (1CH methacryloyl), 125.90 (2CH methacryloyl), 136.72 (2C methacryloyl), 136.99 (C methacryloyl), 166.50 (C methacryloyl), 166.81 (2C methacryloyl). EIMS for $C_{29}H_{44}O_{14}$ calculated 616.2785, found 616.2768, 617.2696 which is a $^{13}$C isotope. Anal. Calc. for $C_{29}H_{44}O_{14}$: C, 56.4; H, 7.3; O, 36.3. Found: C, 56.5; H, 7.4. FIGS. 8 and 9 illustrate the respective NMR spectra of this final product.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structure (I):

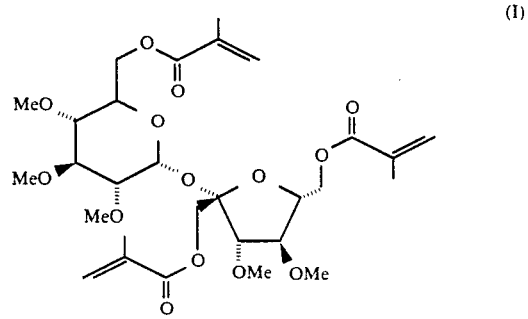

which compound is 1',6,6'-trimethylacryloyl-2,3,3',4,4'-penta-O-methylsucrose.

2. A process for preparing 1',6,6'-trimethylacryloyl-2,3,3',4,4'-penta-O-methylsucrose comprising the steps of:
   (a) adding 15 equivalents of triethylamine to 2,3,3',4,4'-penta-O-methylsucrose to form a mixture;
   (b) adding between 3.5 to 6.0 equivalents of methacryloyl chloride to said mixture;
   (c) stirring said mixture in (b) for about 3 hours at a temperature between 0° C. and 8° C.; and
   (d) isolating 1',6,6'-trimethylacryloyl-2,3,3',4,4'-penta-O-methylsucrose.

* * * * *